United States Patent
Nazzaro

(10) Patent No.: US 12,115,351 B2
(45) Date of Patent: Oct. 15, 2024

(54) SECURE WIRELESS COMMUNICATIONS BETWEEN A GLUCOSE MONITOR AND OTHER DEVICES

(71) Applicant: Insulet Corporation, Acton, MA (US)

(72) Inventor: David Nazzaro, Groveland, MA (US)

(73) Assignee: INSULET CORPORATION, Acton, MA (US)

( * ) Notice: Subject to any disclaimer, the term of this patent is extended or adjusted under 35 U.S.C. 154(b) by 252 days.

(21) Appl. No.: 17/490,372

(22) Filed: Sep. 30, 2021

(65) Prior Publication Data

US 2022/0096750 A1    Mar. 31, 2022

Related U.S. Application Data

(60) Provisional application No. 63/085,822, filed on Sep. 30, 2020.

(51) Int. Cl.
| | |
|---|---|
| G06F 21/62 | (2013.01) |
| A61M 5/142 | (2006.01) |
| A61M 5/172 | (2006.01) |
| H04W 12/03 | (2021.01) |
| H04W 12/06 | (2021.01) |

(52) U.S. Cl.
CPC ...... *A61M 5/1723* (2013.01); *A61M 5/14244* (2013.01); *G06F 21/6245* (2013.01); *H04W 12/03* (2021.01); *H04W 12/06* (2013.01); *A61M 2205/3553* (2013.01)

(58) Field of Classification Search
CPC .. A61M 5/1723; H04W 12/03; G06F 21/6245
See application file for complete search history.

(56) References Cited

U.S. PATENT DOCUMENTS

| | | |
|---|---|---|
| 303,013 A | 8/1884 | Horton |
| 2,797,149 A | 6/1957 | Skeggs |
| 3,631,847 A | 1/1972 | Hobbs |
| 3,634,039 A | 1/1972 | Brondy |

(Continued)

FOREIGN PATENT DOCUMENTS

| | | |
|---|---|---|
| AU | 2015200834 A1 | 3/2015 |
| AU | 2015301146 A1 | 3/2017 |

(Continued)

OTHER PUBLICATIONS

US 5,954,699 A, 09/1999, Jost et al. (withdrawn)

(Continued)

*Primary Examiner* — Simon P Kanaan
(74) *Attorney, Agent, or Firm* — GOODWIN PROCTER LLP

(57) ABSTRACT

The exemplary embodiments may provide a secure framework for devices in a drug delivery system to wirelessly communicate. The secure framework may use encrypted keys to carry credentials and to specify the rights of the devices presenting the credentials. The devices in the drug delivery system present the keys at the time that they wish to wirelessly communicate with other devices in the drug delivery system. The devices receiving such keys, decrypt the keys and verify if the credentials are valid. If the credentials are valid, a wireless communication session between devices may be established.

16 Claims, 12 Drawing Sheets

(56) References Cited

U.S. PATENT DOCUMENTS

| | | |
|---|---|---|
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |

(56) References Cited

U.S. PATENT DOCUMENTS

| | | |
|---|---|---|
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |

(56) References Cited

U.S. PATENT DOCUMENTS

| | | |
|---|---|---|
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |

(56) References Cited

U.S. PATENT DOCUMENTS

| | | |
|---|---|---|
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1* | 11/2013 | Kamen .......... G16H 40/20 600/595 |
| 2013/0338576 A1 | 12/2013 | OConnor et al. |
| 2014/0005633 A1 | 1/2014 | Finan |
| 2014/0200426 A1 | 1/2014 | Taub et al. |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birthwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1* | 9/2015 | Vazquez .......... A61M 5/162 604/67 |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0335409 A1* | 11/2016 | Mensinger .......... G06F 21/6245 |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Linteruer et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |
| EP | 2139382 A1 | 1/2010 |
| EP | 2397181 A1 | 12/2011 |
| EP | 2666520 A1 | 11/2013 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 1571582 B1 | 4/2019 |
| EP | 2897071 B1 | 5/2019 |
| EP | 3607985 A1 | 2/2020 |
| GB | 2443261 A | 4/2008 |
| JP | S51125993 A | 11/1976 |
| JP | 02131777 A | 5/1990 |
| JP | 2004283378 A | 10/2007 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |

(56) References Cited

FOREIGN PATENT DOCUMENTS

| | | |
|---|---|---|
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 05110601 A1 | 5/2004 |
| WO | 2004043250 A1 | 5/2004 |
| WO | 04092715 A1 | 10/2004 |
| WO | 2005051170 A2 | 6/2005 |
| WO | 2005082436 A1 | 9/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A2 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078220 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A2 | 4/2020 |
| WO | 2021011738 A1 | 1/2021 |

OTHER PUBLICATIONS

International Search Report and Written Opinion for the International Patent Application No. PCT/US2022/013470, mailed May 6, 2022, 14 pages.

International Search Report and Written Opinion for the International Patent Application No. PCT/US2022/013473, mailed May 6, 2022, 13 pages.

International Search Report and Written Opinion for the International Patent Application No. PCT/US2022/019079, mailed Jun. 2, 2022, 14 pages.

International Search Report and Written Opinion for the International Patent Application No. PCT/US2022/018453, mailed Jun. 2, 2022, 13 pages.

International Search Report and Written Opinion for the International Patent Application No. PCT/US22/018700, mailed Jun. 7, 2022, 13 pages.

International Search Report and Written Opinion for the International Patent Application No. PCT/US22/019080, mailed Jun. 7, 2022, 14 pages.

International Search Report and Written Opinion for the International Patent Application No. PCT/US22/019664, mailed Jun. 7, 2022, 14 pages.

International Search Report and Written Opinion for the International Patent Application No. PCT/US21/060618, mailed Mar. 21, 2022, 15 pages.

Herrero Pau et al: "Enhancing automatic closed-loop glucose control in type 1 diabetes with an adaptive meal bolus calculator-in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

(56) References Cited

OTHER PUBLICATIONS

International Search Report and Written Opinion for the International Patent Application No. PCT/US2022/012896, mailed Apr. 22, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Preliminary Report on Patentability in PCT/US2021/052855, mailed on Apr. 13, 2023, 8 pages.
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.
"Read NFC Tags with an iPHone App on iOS 11", GoToTags, Sep. 11, 2017, web <https://gototags.com/blog/read-nfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.

International Search Report and Written Opinion for Application No. PCT/US2019/030652, Sep. 25, 2019, 19 pages.
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, mailed Jun. 2, 2021, 15 pages.
Farkas et al. ""Single-Versus Triple-Lumen Central Catheter-Related Sepsis: A Prospective Randomized Study in a Critically Ill Population"" The American Journal of Medicine Sep. 1992vol. 93 p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A ""Microbial Contamination Of Haemodialysis Catheter Connections"" Journal of Renal Care, European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Schlegel et al, "Multilumen Central Venous Catheters Increase Risk for Catheter-Related Bloodstream Infection: Prospective Surveillance Study".
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 mailed Jul. 16, 2010.
International Search Report and Written Opinion in PCT/US2008/079641 dated Feb. 25, 2009.
Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et. al., "Clinical Performance of an In line Ex-Vivo Point of Care Monitor: A Multicenter Study," Clinical Chemistry 48: 11, pp. 2030-2043, 2002.

(56) References Cited

OTHER PUBLICATIONS

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.

International Preliminary Report on Patentability for the International Patent Application No. PCT/US2019/053603, mailed Apr. 8, 2021, 9 pages.

International Search Report and Written Opinion for the International Patent Application No. PCT/US2019/053603, mailed Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, mailed May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

International Search Report and Written Opinion for the International Patent Application No. PCT/US2020/052125, mailed Aug. 12, 2020, 15 pages.

International Search Report and Written Opinion for the International Patent Application No. PCT/US2020/050332, mailed Sep. 12, 2020, 12 pages.

European Patent Office, "Notification of Transmittal of the ISR and the Written Opinion of the International Searching Authority, or the Declaration," in PCT Application No. PCT/GB2015/050248, Jun. 23, 2015, 12 pages.

International Search Report and Written Opinion for the International Patent Application No. PCT/US2021/012246, mailed Apr. 13, 2021, 15 pages.

International Search Report and Written Opinion for the International Patent Application No. PCT/US2021/013639, mailed Apr. 28, 2021, 14 pages.

International Search Report and Written Opinion for the International Patent Application No. PCT/US2020/063326, mailed May 3, 2021, 17 pages.

European Search Report for the European Patent Application No. 21168591, mailed Oct. 13, 2021, 04 pages.

International Search Report and Written Opinion for the International Patent Application No. PCT/US2021/041954, mailed Oct. 25, 2021, 13 pages.

International Search Report and Written Opinion for the International Patent Application No. PCT/US2021/052855, mailed Dec. 22, 2021, 11 pages.

International Search Report and Written Opinion for the International Patent Application No. PCT/US2021/047771, mailed Dec. 22, 2021, 11 pages.

International Search Report and Written Opinion for the International Patent Application No. PCT/US2021051027, mailed Jan. 7, 2022, 16 pages.

International Search Report and Written Opinion for International application No. PCT/US2021/052372, mailed on Jan. 26, 2022, 15 pages.

* cited by examiner

SECURE WIRELESS COMMUNICATIONS BETWEEN A GLUCOSE MONITOR AND OTHER DEVICES

CROSS-REFERENCE TO RELATED APPLICATIONS

This application claims the benefit to U.S. Provisional Application No. 63/085,822, filed Sep. 30, 2020, the entire contents of which are incorporated herein by reference in their entirety.

BACKGROUND

A typical conventional on-body insulin delivery system may include an insulin pump and a continuous glucose monitor (CGM). The insulin pump may contain insulin for delivery to a user under the control of a control algorithm. The insulin pump may be positioned on the body of the user. The CGM monitors blood glucose levels of the user on an on-going basis. The CGM, like the insulin pump, may be positioned on the body of the user. The insulin drug delivery system may also include a management device, like a dedicated handheld device or a smartphone, that runs a management application.

There may be certain communication limitations with such a conventional on-body insulin delivery system. For example, the CGM may require a Near Field Communication (NFC) capability to initialize the CGM and begin communications with the management device. For the case where the management device is a smartphone of a user that is not NFC capable, the phone is not able to initialize the CGM. In addition, such a conventional insulin delivery system may require that the management device act as an intermediary for communications between the insulin pump and the CGM. For instance, if the insulin pump wishes to read blood glucose level values stored in the CGM, the insulin pump may need to ask the management device to get the blood glucose level values from the CGM and return the retrieved blood glucose level values to the insulin pump. Due to security concerns, additional devices are not permitted to wirelessly communicate with the insulin pump or CGM.

SUMMARY

In accordance with an inventive aspect, a medicament delivery device includes a medicament supply and a pump for pumping the medicament from the medicament supply to a user. The device also includes a wireless transceiver for transmitting and receiving wireless communications. The device further includes a processor configured to receive a secure package from a requesting device via a wireless connection and extract contents of the secure package, including a key. The processor is further configured to validate the key as valid or not. Where the key is valid, wireless communications with the requesting device are permitted, and where the key is not valid, wireless communications with the requesting device are not permitted.

The processor may be further configured to generate an additional key for the medicament delivery device to wirelessly communicate with an additional device. The processor may be configured to generate a secure package containing the key and to send the secure package wirelessly to the additional device to request wireless communications with the additional device. The extracting of the contents of the secure package may involve at least one of decrypting the secure package, applying an inverse hash function to the secure package or reversing an obfuscation of the secure package. The extracting of the contents of the secure package may extract the key from the secure package and/or a timestamp. The validating the key may entail using the timestamp to determine whether the key has expired. The extracting of the contents of the secure package may involve extracting information regarding rights to be granted to the requesting device as to wireless communications. The requesting device may be one of a glucose monitor, a wearable device or a mobile computing device.

In accordance with an inventive aspect, an on-body medical device includes a wireless transceiver for transmitting and receiving wireless communications. The device also includes a processor configured to receive a secure package from a requesting device via a wireless connection and extract contents of the secure package, including a key. The processor is further configured to validate the key as valid or not. Where the key is valid, the processor permits wireless communications with the requesting device. Where the key is not valid, the processor does not permit wireless communications with the requesting device.

The extracting of the contents of the secure package may include at least one of decrypting the secure package, applying an inverse hash function to the secure package or reversing an obfuscation of the secure package. The extracting of the contents of the secure package may include extracting the key from the secure package and/or extracting a timestamp. The validating of the key may entail using the timestamp to determine whether the key has expired. The extracting of the contents of the secure package may include extracting information regarding rights to be granted to the requesting device as to wireless communications. The on-body medical device may be a glucose monitor or a drug delivery device.

In accordance with an inventive aspect, a device includes a wireless transceiver for transmitting and receiving wireless communications and a processor. The processor is configured to generate a secure package that is encrypted, hashed and/or obfuscated. The secure package contains a key for wireless communications. The processor also is configured to send the secure package wirelessly to request wireless communication to a target device. The target device is one of a drug delivery device, a biometric sensor, or a manager of a drug delivery device.

The secure package may contain a timestamp for the key. The secure package may contain identity information for the device. The secure package may contain information regarding the rights to be granted to the device regarding wireless communications.

DETAILED DESCRIPTION

Figure 1A:
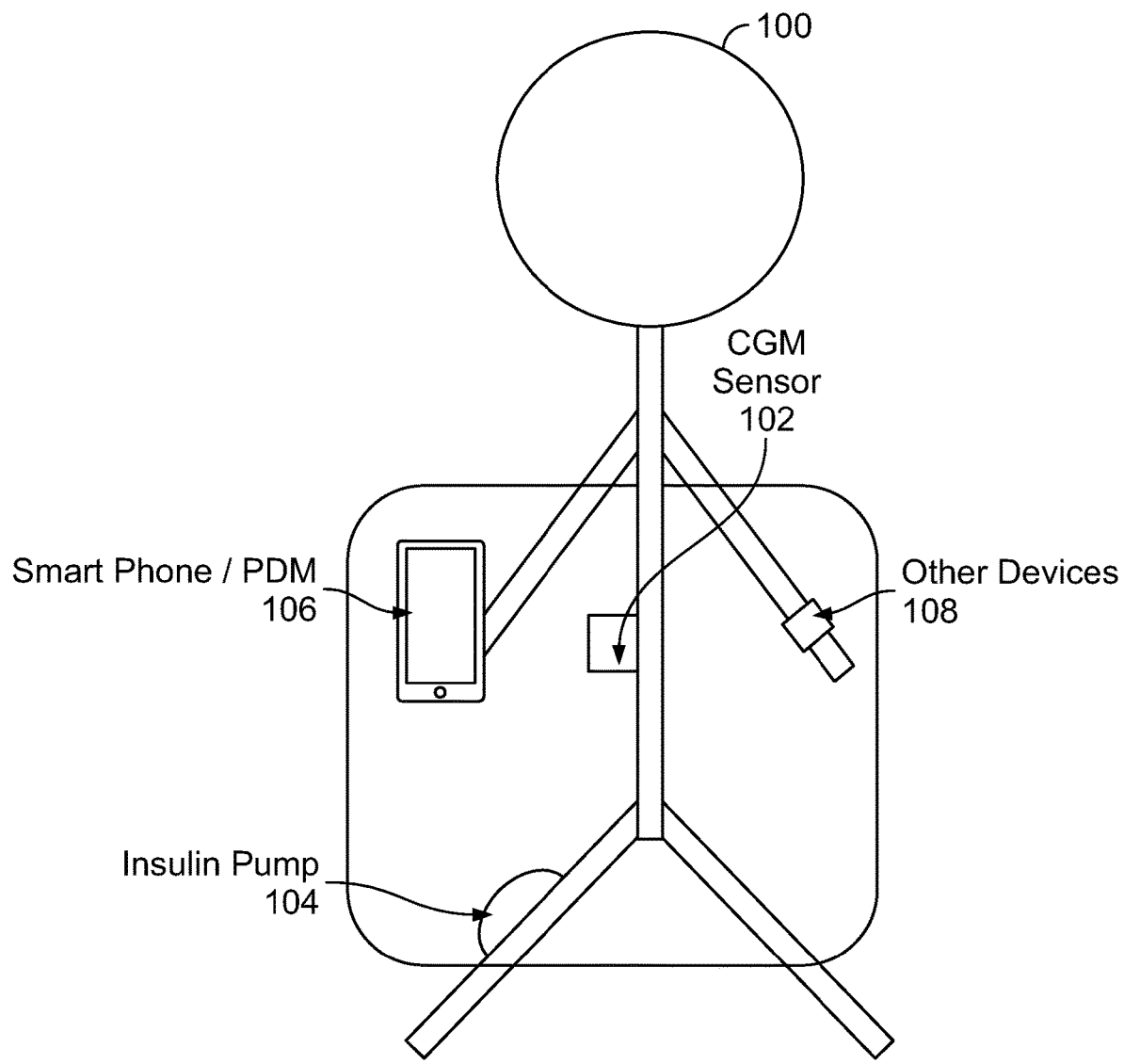
FIG. 1A depicts a diagram of a user with multiple illustrative devices for use in an exemplary embodiment.

The exemplary embodiments may provide a secure framework for devices in a drug delivery system to wirelessly communicate. The secure framework may use secure keys to carry credentials and to specify the rights of the devices presenting the credentials. The devices in the drug delivery system present the secure keys at the time that they wish to wirelessly communicate with other devices in the drug delivery system. The devices receiving such secure keys, process the keys and verify if the credentials are valid. If the credentials are valid, a wireless communication session between devices may be established. If not, a wireless communication session is not permitted.

The exemplary embodiments may eliminate the need for the management device of a drug delivery system to act as an intermediary for wireless communications among devices in the drug delivery system. Thus, an medicament pump may wirelessly communicate directly with the CGM. This may be helpful in creating a closed loop control system where the medicament pump receives blood glucose level readings directly from the CGM via wireless communications and feeds the received blood glucose level readings into the control algorithm of the medicament pump. In such circumstances, additional devices are unnecessary when the medicament pump and CGM are operating in a closed loop. After the medicament pump is activated the medicament pump and the CGM may operate in a closed loop fashion without other devices.

An additional benefit of use of the secure framework is that it allows additional devices to communicate with the CGM and medicament pump. For example, a wearable device, such as a smart watch, smart ring or smart bracelet, may communicate with the CGM or medicament pump if the wearable device contains the proper credentials. The wearables may provide some of the functionality that is otherwise provided exclusively by the management device. This may be easier from some users as opposed to needing to carry the management device as the users move about. Moreover, the form factors of the wearable devices may make them more convenient than the management device when performing activities such as exercising. Still further, the wearable device may be more discrete than the management device. A user can look at a wearable for a current blood glucose reading more discretely than a larger management device that is handheld. Also, since the wearable is worn on-body, the user does not have to be concerned with leaving the wearable behind once the wearable is secured to the user.

The ability of additional devices to be validated and communicate with the medicament pump or CGM also expands the possible configurations of the drug delivery system. For example, biometric sensors, like blood pressure sensors, heart rate sensors, galvanic sensors and accelerometers, if not already built into the medicament pump or CGM, may be set up to wirelessly communicate with the medicament pump and provide useful inputs to the control algorithm for the medicament pump. Also, the CGM may output blood glucose level readings to smart watches, tablet computers and other devices for display and analysis.

The exemplary embodiments are described below relative to a drug delivery system that delivers a medicament, such as insulin, a GLP-1 agonist or pramlintide. As a result, in the discussion below the drug delivery device is an insulin pump, and the sensor is a CGM. Nevertheless, it should be appreciated that the secure framework may also be used with other types of drug delivery systems that deliver agents such as pain management agents, chemotherapy agents, antibiotics, therapeutic agents, etc., and that deploy different biometric sensors as part of a continuous biometric meter or CBM.

FIG. 1A depicts an illustrative user 100 of a glucose monitor 102 with a number of devices that are being either carried by the user 100 or are attached to the user 100. The devices 102, 104, 106 and 108 may all be part of a medicament delivery system. The depiction is intended to be merely illustrative and not limiting. The glucose monitor 102 is a sensor that is an on body device that is affixed to the user 100. The glucose monitor 102 provides regular blood glucose level readings via a sensor placed under the skin of the user 100. The glucose monitor 102 may be a CGM. The user 100 has a management device realized as a smartphone or a personal diabetes monitor (PDM) 106. The PDM 106 is a handheld device that is dedicated for use with an insulin pump 104. An example of the insulin pump 104 is the Omnipod from Insulet Corporation. The smartphone/PDM 106 may be held by the user 100 or be in the possession of the user, such as on the user's belt or in the user's pocket. The insulin pump 104 may be secured to the user, such as on a user's abdomen or on the user's leg, as shown in FIG. 1A. The insulin pump 104 is a medicament delivery device that delivers insulin to the user. The insulin pump 104 may include a needle, a cannula and tubing or the like for providing a pathway for delivering the drug (e.g., insulin) to the user 100. In this example, an example of one of the other devices 108 is shown being worn on the wrist of the user 100. The other devices 108 may include a wearable device, such as a smart watch, a smart bracelet or a smart ring. That said, the other devices 108 need not include a wearable device but more generally may include a device that is capable of wireless communication and is able to participate in the secure framework for wireless communication as will be described in more detail below. The other devices 108 may include an NFC-enabled and/or BLE-enabled device.

Figure 1B:
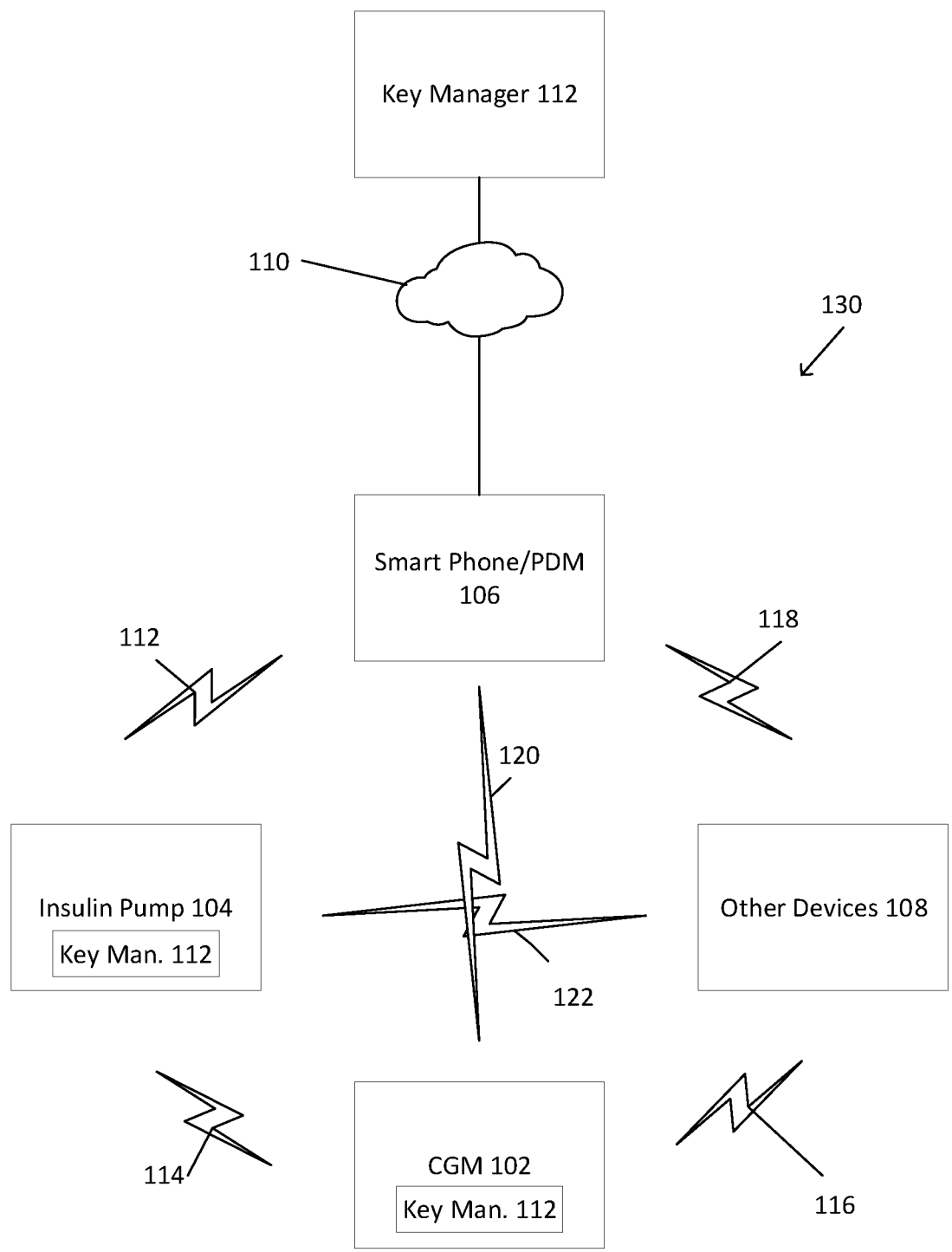
FIG. 1B depicts a block diagram illustrating communication links for devices in a drug delivery system of an exemplary embodiments.

FIG. 1B depicts a block diagram of the medicament delivery system 130 for the components 102, 104, 106 and 108 shown in FIG. 1A. The other devices 108 are intended to represent any device that is capable of wirelessly communicating with the other components in the drug delivery system. The other devices 108 may be a wearable device, a sensor, a fob, a tablet computer, a mobile computing device, a desktop computing device, an instrument with wireless capability or the like. In exemplary embodiments, wireless connections 112, 114, 116, 118, 120 and 124 may be established between pairs of these components in accordance with the secure framework. This enables each of the components 102, 104, 106 and 108 to wirelessly communicate with the other components. The depiction in FIG. 1B depicts total wireless connectivity between each pair of the components 102, 104, 106 and 108. In some exemplary embodiments, only a subset of the wireless connections 112, 114, 116, 118, 120 and 122 need to be established.

As can be seen in FIG. 1B, there is no longer the need for the smart phone/PDM 106 to act as an intermediary for wireless communications. Thus, for example, the insulin pump 104 may directly communicate with the CGM 102 via a wireless connection 114. As was mentioned above, the direct wireless connection 114 between the CGM and the insulin pump 104 may facilitate a control loop where blood glucose level readings from the CGM 102 are fed to the insulin pump 104 and serve as input to a control algorithm of the insulin pump 104 that adjusts insulin delivery amounts and/or timing based on the blood glucose level readings. In addition, additional devices, like other devices 108, may communicate with the devices 102, 104 and 106 in the medicament delivery system 130. As a result, the other devices 108 may, for example, display blood glucose level readings or insulin deliver history information or issue commands to the insulin pump 104 in some exemplary embodiments, such as when operating in an open-loop control fashion.

The smart phone/PDM 106 may have a connection to a network 110, such as an Internet connection, a virtual private network (VPN), a Local Area Network (LAN), a cellular phone network or a combination thereof. The connection to the network 110 provides access to a key manager 112. The key manger 112 may be resident on a server and may be provided as a cloud service in some exemplary embodiments. The key manager 112 alternatively may be resident locally, such as on the insulin pump 104 or on the CGM 112 as shown in. The key manager 112 is responsible for generating keys that are for use in the secure framework. As will be described in more detail below, the key manager 112 is responsible for generating keys that are used to establish wireless connections, like wireless connections 112, 114, 116, 118, 120 and 122, in the medicament delivery system 130. The keys may be provided upon request of the smart phone/PDM 106, insulin pump 104, CGM 102, or other devices 108.

As was discussed above, the exemplary embodiments may use devices other than a smartphone/PDM 106 to initialize an uninitialized glucose monitor 106 or to awaken a sleeping glucose monitor 106. The other devices 108 may include, for example, wearables like a smartwatch or ring, a tablet, a fob, a smart pager, a notebook computer, a badge or a tag. The other devices 108 may be able to communicate using the desired wireless protocol (e.g., NFC) such that it can perform the functionality described above. The secondary or other device 108 may have a form factor (e.g. size, weight, etc.) that lends itself to convenient use in interacting with the glucose monitor 106, or insulin pump 104, or CGM 102.

Figure 2A:
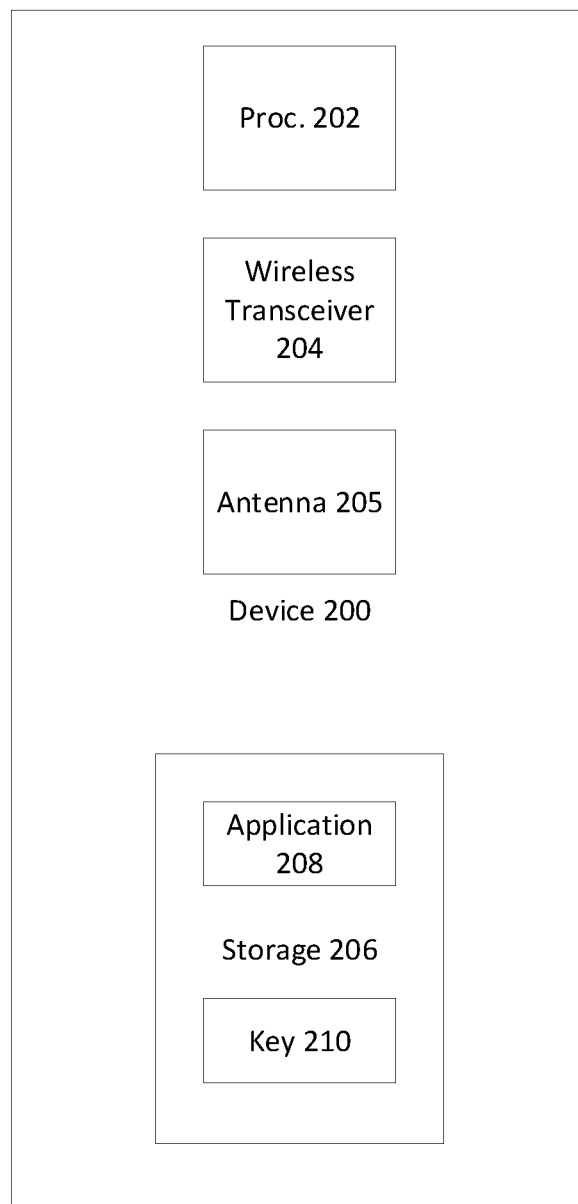
FIG. 2A depicts a block diagram of an illustrative device in the drug delivery system of an exemplary embodiment.

FIG. 2A shows a generalized block diagram of components of a device 200 that participates in wireless communication with at least one component in a drug delivery system like medicament delivery system 130 depicted in FIG. 1B. CGM 102, insulin pump 104, smartphone/PDM 106 and other devices 108 are examples of such a device 200. The device 200 includes a processor 202 like a Central Processing Unit (CPU), a Graphics Processing Unit (GPU), an Application Specific Integrated Circuit, a Field Programmable Gate Array (FPGA), a System on a Chip (SoC), or other processing component. The processor 202 may execute computer programming instructions, like application 208. The application 208 may contain instructions for performing the functionality described herein relating to establishing wireless connections, generating secure packages with keys and validating keys. Each device that wishes to participate in a secure framework must run the application 208 or have equivalent functionality performed by another program, applet, module, library, routine, object, method function or the like. Wireless transceiver 204 facilitates wireless communications by transmitting and receiving communications via an antenna 205. The wireless transceiver may communicate using one or more wireless protocols, such as the Bluetooth wireless protocol, the Bluetooth Low Energy (BLE) protocol, the WiFi (IEEE 802.11) wireless protocol, the Near Field Communication (NFC) wireless protocol, the Wireless Body Area Network (WBAN) wireless protocol (IEEE 802.15.6) or other wireless protocol. Multiple wireless transceivers for different protocols may be provided in some embodiments.

A storage 206 may be provided for storing computer programs, computer program instructions and/or data. The storage may store the application 208 and a secure key 210 that is used in the secure framework described herein. The storage may include Random Access Memory (RAM), Read Only Memory (ROM), flash memory, magnetic disk storage, optical disk storage, solid state storage, computer-readable storage media, registers or the like.

Figure 2B:
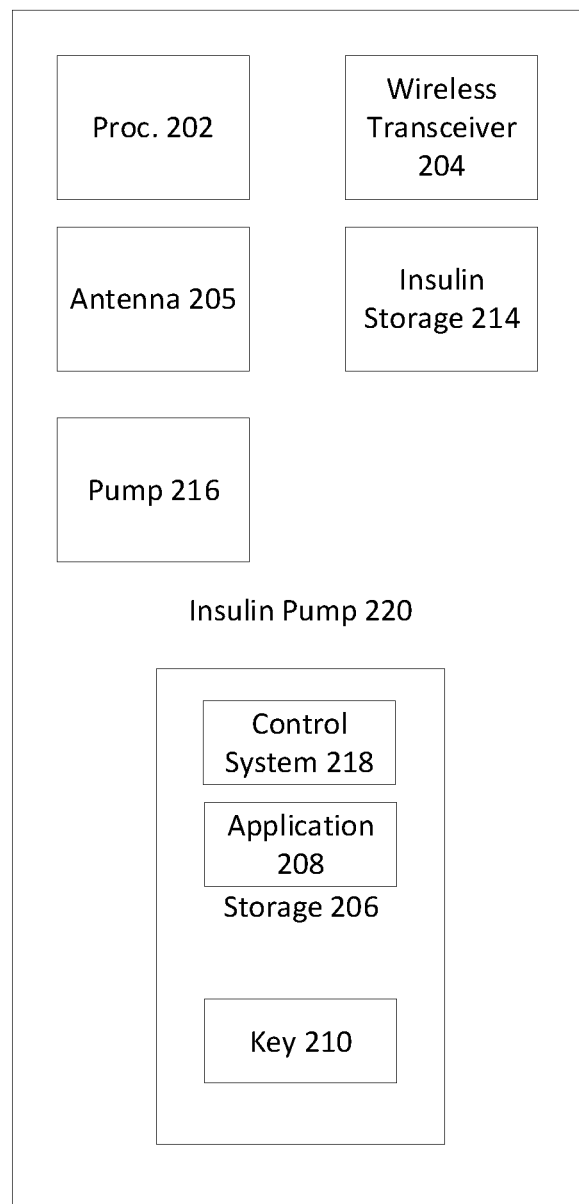
FIG. 2B depicts a block diagram of a medicament pump of an exemplary embodiment.

FIG. 2B depicts a more detailed block diagram of an insulin pump 220 of an exemplary embodiment. Like the device 200 (which, again, may represent an insulin pump), the insulin pump 220 contains a processor 202, a wireless transceiver 204, an antenna 205, a storage 206, application 208, a secure key 210 as described above relative to FIG. 2A. The insulin pump 220 also contains an insulin storage 214 for storing the insulin to be delivered to the user and a pump 216 for pumping the insulin out of the insulin storage 214 to the user. In addition, the storage 206 stores computer programming instructions for implementing the control system functionality 218. These instructions 218 implement the control algorithm that controls delivery of insulin to the user.

Figure 3:
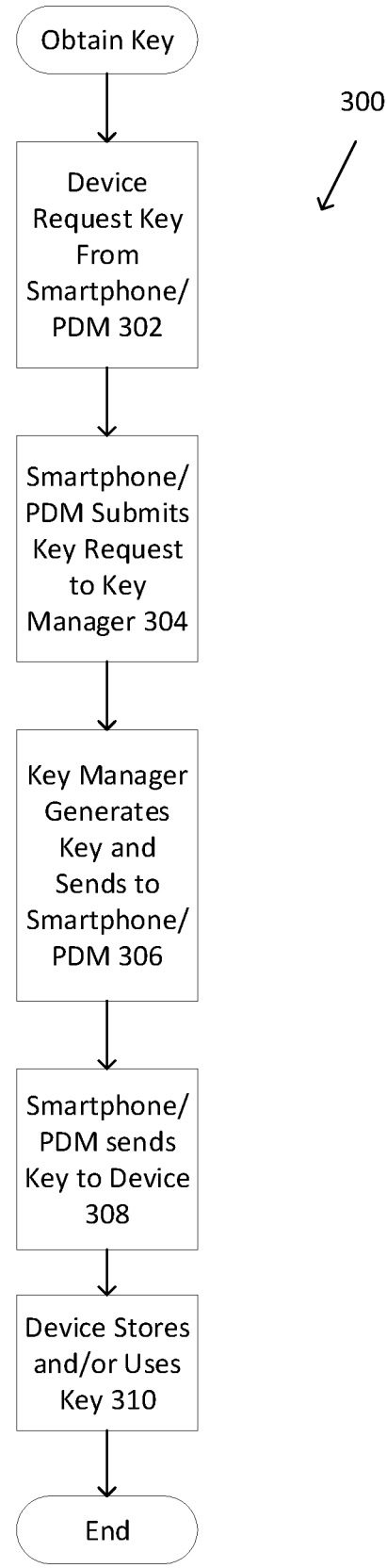
FIG. 3 depicts a flowchart of steps that may be performed in an exemplary embodiment to obtain a secure key for wireless communication.

FIG. 3 depicts a flowchart of steps that may be performed in an exemplary embodiment to obtain a secure key for wireless communication. The process may begin with a request from a device for a secure key that is sent to the smartphone/PDM 106 (302). Alternatively, no request may be required, or all devices may be provided secure keys at boot time in alternative embodiments. The smartphone/PDM 106 is responsible for getting such secure keys and distributing the secure keys to the devices 102, 104, 106 and 108. The smartphone/PDM submits the request to the key manager 112 (304). The key manager 112 generates the secure key and sends the secure key to the smartphone/PDM 106 (306). The generation may entail retrieving the secure key from secure storage or generating the secure key on demand. The smartphone/PDM 106 sends the secure key to the requesting device (308). The requesting device may store the secure key and/or use the secure key once received to establish wireless communication with one of the devices 102, 104, 106 or 108 (310).

Figure 4A:
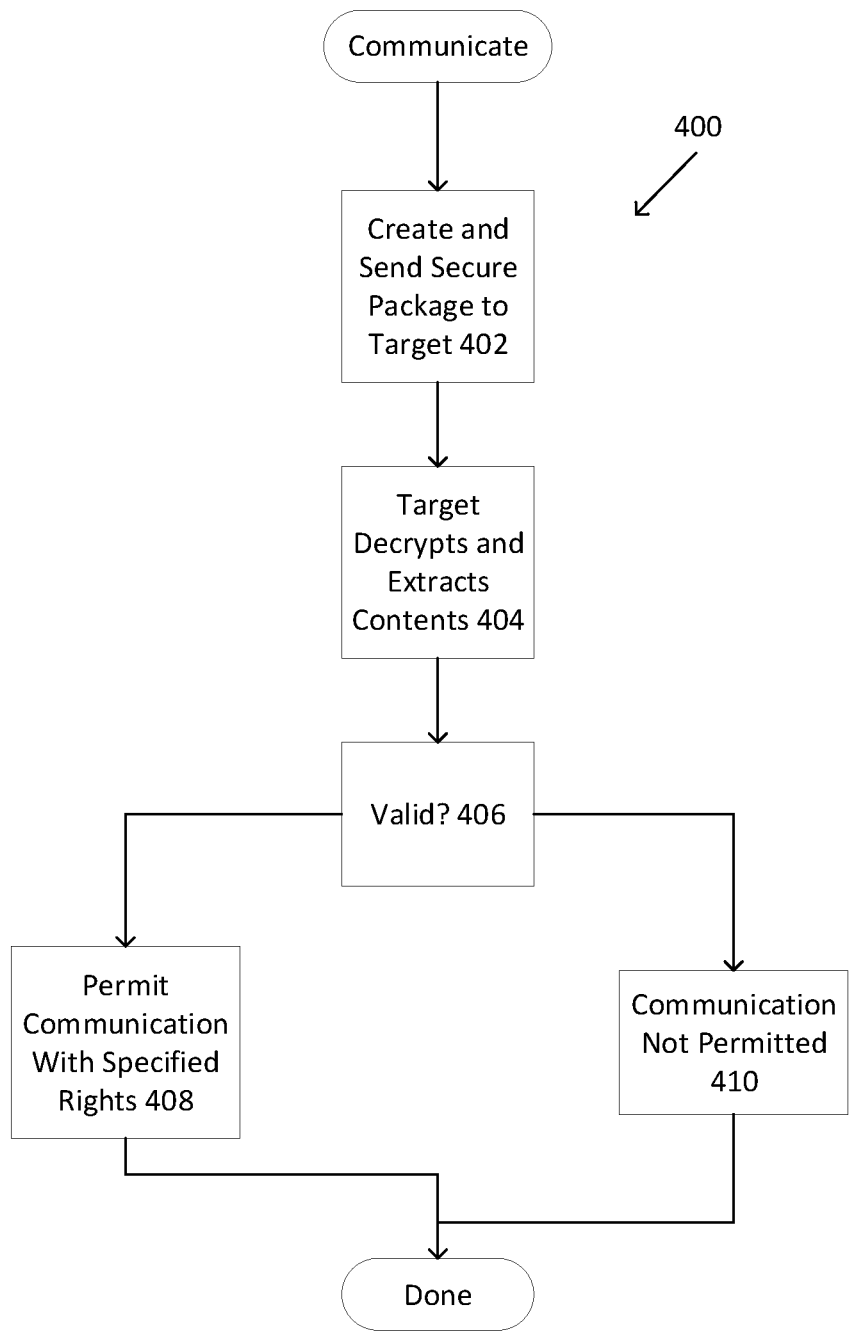
FIG. 4A depicts a flowchart of illustrative steps that may be performed to get permission to wirelessly communicate in an exemplary embodiment.
Figure 4B:
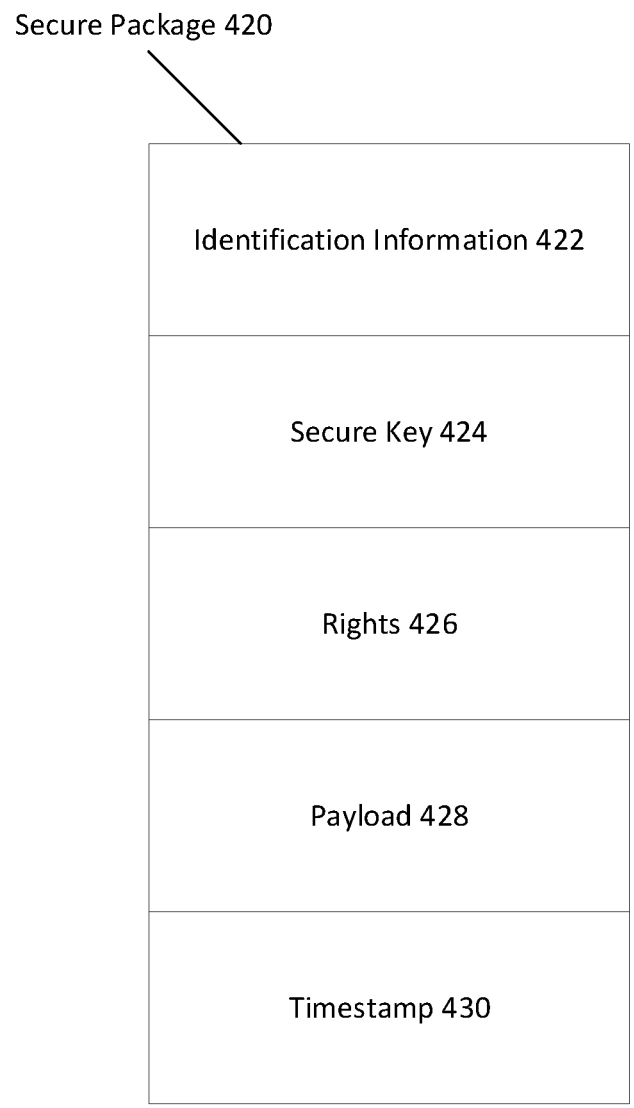
FIG. 4B depicts a diagram of elements of a secure package in an exemplary embodiment.

FIG. 4A depicts a flowchart 400 of illustrative steps that may be performed to establish a wireless communication connection using a secure key. The requesting device that wishes to communicate creates and sends a secure package to the target device (402). FIG. 4B shows an example of illustrative contents for the secure package 420. The package may be secure in that it may be hashed, encrypted and/or otherwise obfuscated to ensure that an unauthorized listener cannot determine the contents of secure package 420. The secure package may contain identification information 422 for the requesting device. The secure package 420 may contain a secure key 424. The secure key 424 may be an encrypted value that serves as a credential. The secure package 420 may also contain information regarding the privileges of the requesting device 426. These privileges might be, for example, a read privilege where the requesting device may read information from the target device but not modify any information. The rights 426 may specify a write privilege, which enables the requesting device to write information in the storage of the target device. The rights 426, in some instances, may specify both read and write privileges for a requesting device. It should be appreciated that the rights may specify other parameters, such as what information types or particular data may be viewed or modified. The rights 426 may specify whether the requesting device is able to send commands to the target device. A payload 428 may be provided as part of the secure package 420. The payload 428 may contain messages, data, commands or other information that is to be sent to the target device. The secure package 420 may also include a timestamp 430. The timestamp 430 may specify how long the secure key 424 is good for or when the key 424 was created. After expiration of a designated time period, the secure key 424 may no longer be valid for use.

After the secure package 420 is sent from the requesting device to the target device (402), the target device decrypts and otherwise reverses the obfuscation of the secure package 420. The target device may have a suitable decryption key, reverse hash function or the like to perform the decryption and/or obfuscation. The target device extracts the contents of the secure package (404). The extraction may include decrypting the secure key 424. The target device may check whether the key 424 is valid (406). The target device possesses knowledge of what a decrypted key value should be and can check whether the decrypted value is correct and valid. Moreover, the target device may use the timestamp 430 to check whether the key 424 has expired as part of checking the validity of the key 424. If the key is determined to be valid, a connection with the requesting device is permitted (408). The requesting device may have the privileges specified by the rights 426. If the key is determined to be invalid, the request to establish a connection is denied by the target device so that wireless communication is not permitted (410). The functionality specified in the flowchart 400 may be realized as part of the application 208.

This ability provided by the secure framework for additional devices to wirelessly communicate with other components in the drug delivery system may help address the problem where a smartphone cannot initialize a CGM because the smartphone lacks NFC capability. With the secure framework another device that has NFC capability may be used to initialize or activate the CGM, or in some cases, the insulin pump.

Figure 5A:
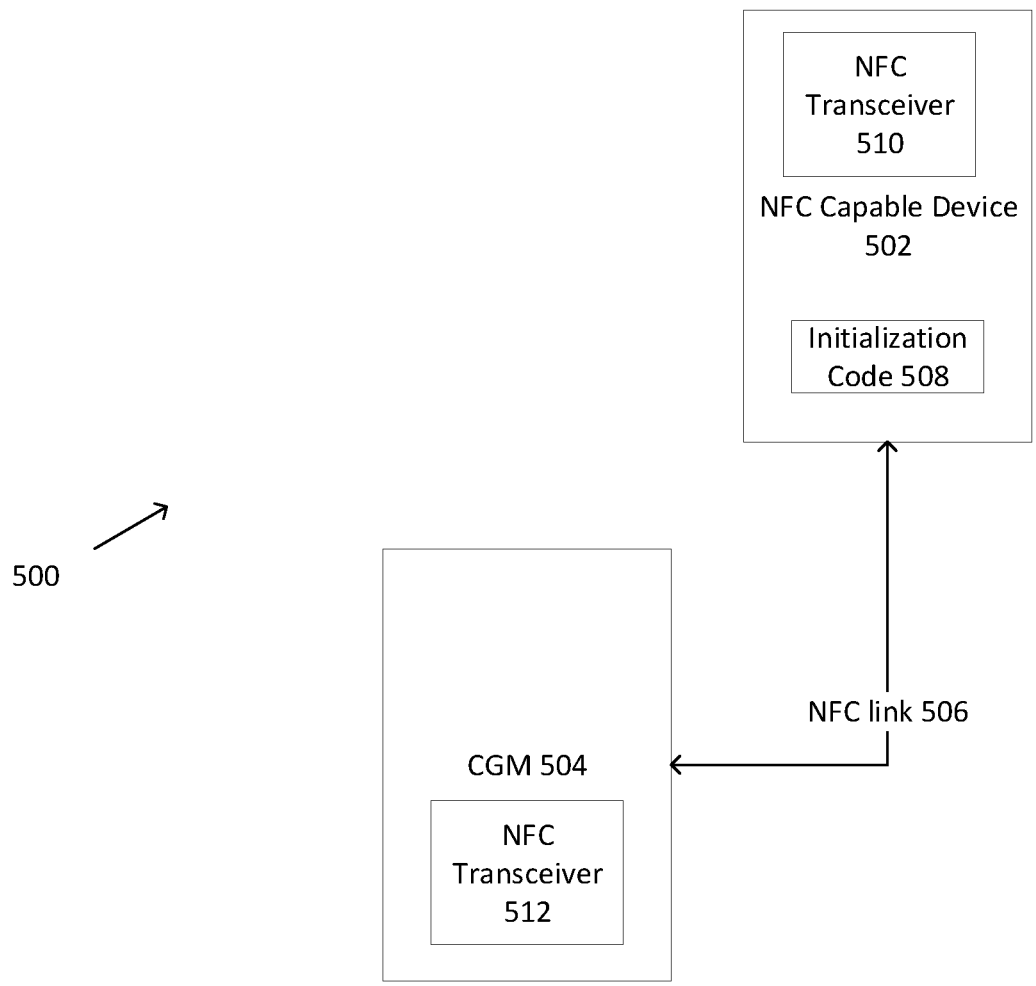
FIG. 5A depicts a block diagram showing how an NFC capable device may initialize a CGM in an exemplary embodiment.
Figure 5B:
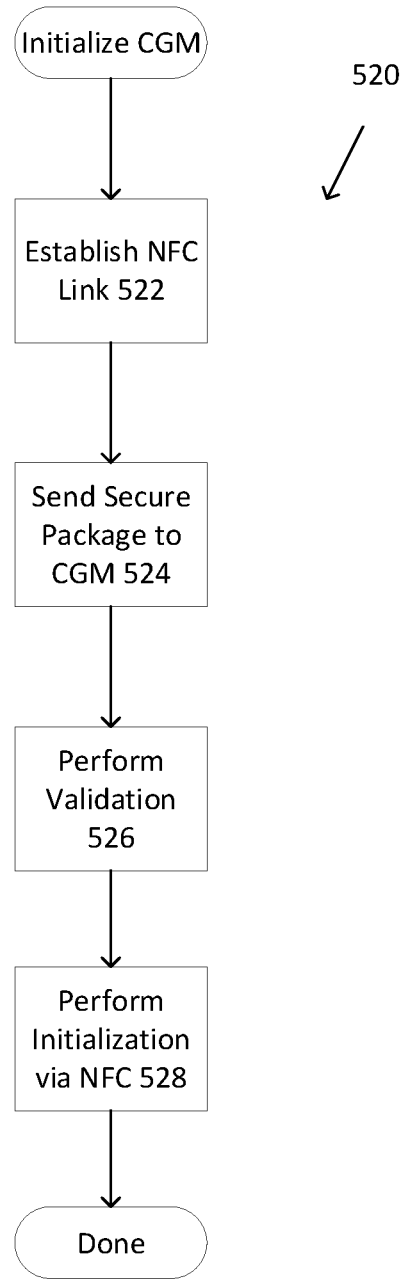
FIG. 5B depicts a flowchart of illustrative steps that may be performed to initialize a CGM with an NFC capable device in an exemplary embodiment.

FIG. 5A depicts a diagram 500 showing an instance in an exemplary embodiment wherein an NFC-capable device 502, e.g., a smartwatch, is used in initializing and awakening (or activating) the CGM 504. The process begins as shown in the flowchart 520 of FIG. 5B. Initially, an NFC link 506 is established between the NFC-capable device 502 and the CGM 504 by placing the NFC-capable device 502 in close proximity with the CGM 504 (522). The NFC transceivers 510 and 512 in the NFC-capable device 502 and the CGM 504 automatically establish the NFC link 506 when placed in proximity with each other. The NFC-capable device 502 then sends a secure package like the secure package 420 that was described with reference to FIG. 4B to the CGM 504 (524). The CGM 504 performs validation of the key as described above relative to FIG. 4A (526). Since the NFC-capable device 502 has a valid key, the communication session is allowed. The NFC-capable device 502 has initialization code 508 that permits it to take the necessary steps via the NFC link 506 to initialize the CGM 504 (528). This initialization code 508 may be like that found on a conventional NFC capable smartphone which is configured to enable initialization or activation of the CGM 504. Once initialized, the CGM 504 is free to communicate with other devices. An identical operation may be performed with an insulin pump having an NFC transceiver.

Figure 6:
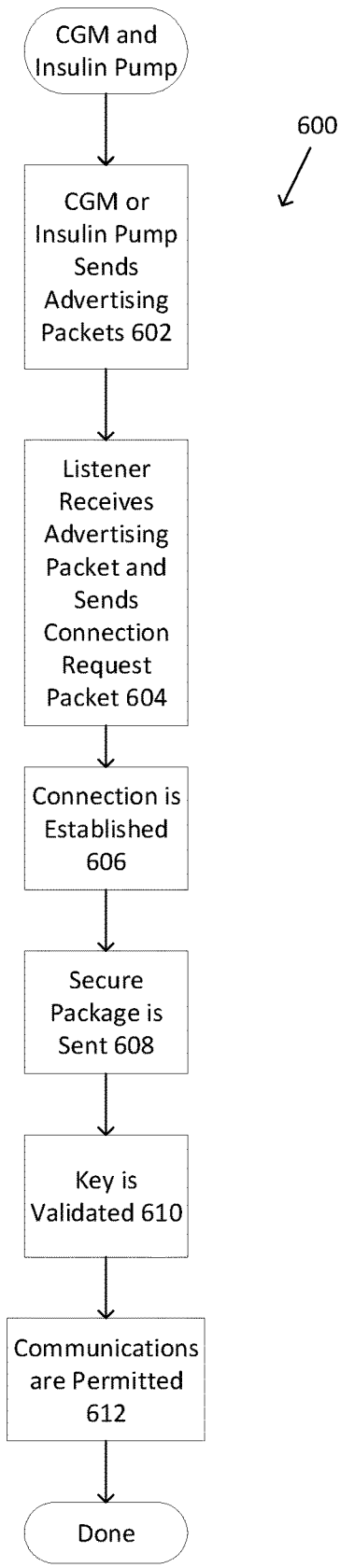
FIG. 6 depicts a flowchart of illustrative steps that may be performed to create a wireless connection between a medicament pump and a CGM in an exemplary embodiment.

As was mentioned above, one advantage provided by the secure framework is that the CGM 102 is able to wirelessly communicate with the insulin pump 104. FIG. 6 provides a flowchart 600 of illustrative steps that may be performed for the CGM 102 and the insulin pump 104 to communicate via BLE. With BLE, the pairing process begins with a device sending out advertising packets on advertising channels. BLE uses 40 channels that are separated in the frequency domain. Three of these channels are designated for advertising. In this example, either the CGM 102 or the insulin pump 104 sends out advertising packets (602). This device is known as the peripheral device or the "peripheral." The other device 102 or 104 listens and receives the advertising packets. The listening device is known as the central device or the "central." The central sends out a connection request packet (604) to the peripheral. A connection is then established (606). However, in the secure framework, the peripheral must present a valid key to continue to wirelessly communicate. To that end, a secure package is sent from the peripheral to the central (608). The key is extracted and validated (610) as has been described above. Wireless communications via BLE between the CGM 102 and the insulin pump are then permitted (612).

Figure 7:
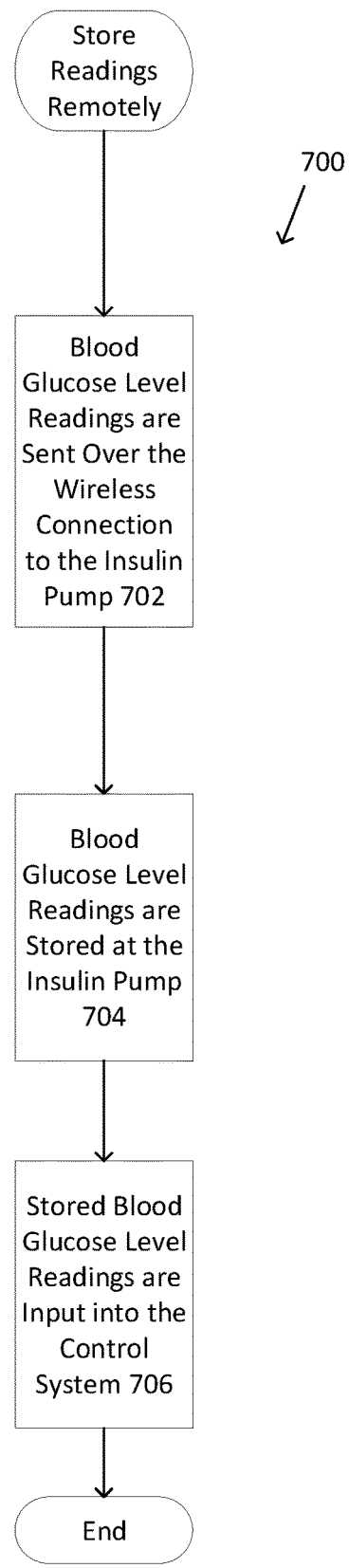
FIG. 7 depicts a flowchart showing illustrative steps that may be performed to store blood glucose level readings at a medicament pump in an exemplary embodiment.

As was mentioned above, the wireless connection between the CGM 102 and insulin pump 104 may be used to realize closed loop control of insulin delivery to the user 100 without involvement of other devices. FIG. 7 provides a flowchart 700 of how the wireless connection for realizing such closed loop control is used. The CGM 102 generates blood glucose level readings. These readings are sent over the wireless connection from the CGM 102 to the insulin pump 104 (702). The blood glucose level readings may be stored at the insulin pump 104 in storage (704). The stored blood glucose level readings may then be used as input into the control system (706). CGM 102 or insulin pump 104 may optionally transmit the blood glucose level readings to other devices for display or tracking purposes. Additionally, the insulin pump 104 may similarly transmit data around insulin delivery (e.g., amount and/or timing of insulin delivered, as basal or bolus amounts, amount of "insulin on board," amount of insulin remaining in reservoir, amount of insulin used, amount of battery charge remaining, estimated expiration of insulin pump 104 based on factors such as amount of insulin remaining in reservoir and/or amount of energy remaining in batteries on insulin pump).

Another benefit of the secure framework is that it allows different devices to have different rights. It may be desirable for security purposes to limit the rights of some devices. One example of this is that a device may only have read rights (viewing rights). For instance, a requester may be granted viewing rights from a target but not write privileges. Hence, the requester can only view information from the target but cannot change values stored on the target or issue commands to the target. Thus, for example, a device may request viewing privileges to receive blood glucose level readings from the CGM 102. Similarly, a device may be granted viewing rights from the insulin pump 104, but not write (or command) privileges. Hence, the requester can only view certain data (such as that identified in the preceding paragraph), but cannot change values stored on the insulin pump 104 or issue commands to the insulin pump 104.

Figure 8:
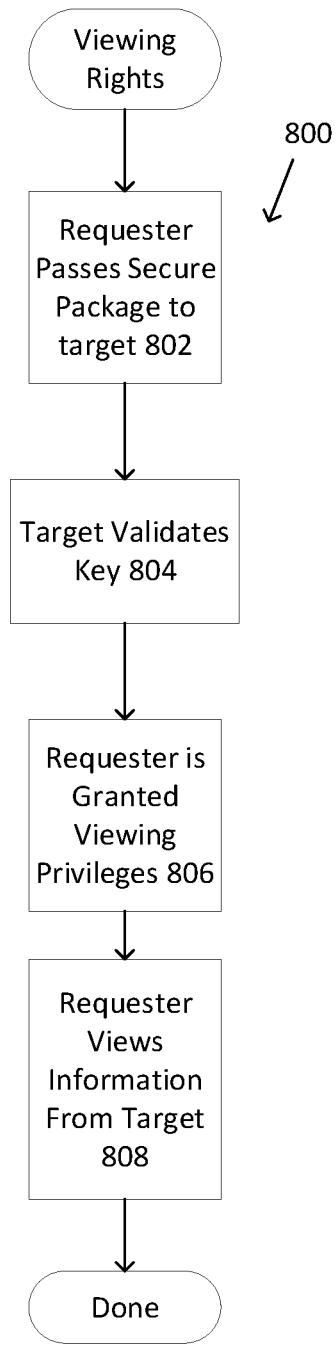
FIG. 8 depicts a flowchart showing illustrative steps that may be performed to obtain viewing rights from a CGM in an exemplary embodiment.

FIG. 8 show a flowchart 800 of illustrative steps that may be performed in such an instance. Initially, the device that is the requester passes a secure package to the device that is the target (802). The secure package contains a valid key that has not expired and specifies the rights as read privileges ("viewing privileges"). The target validates the key as discussed above (804). The requester is granted viewing privileges (806). The requester may then view information from the target (808).

While the present invention has been described with reference to exemplary embodiments herein, those skilled in the art will appreciate that various changes in form and detail may be made without departing from the intended scope as defined in the appended claims.

The invention claimed is:

1. A device comprising:
a wireless transceiver for transmitting and receiving wireless communications;
a processor configured to:
transmit receive a secure package to an uninitialized glucose monitor via a wireless connection;
extract contents of the secure package, including an initialization code and a key;
validate the key as valid or not;
where the key is valid,
permitting wireless communications with the glucose monitor,
validate the initialization code as valid or not,
where the initialization code is valid, initialize the glucose monitor, and
where the initialization code is not valid, not initialize the glucose monitor; and
where the key is not valid, not permitting wireless communications with the glucose monitor.

2. The device of claim 1, wherein the processor is further configured to generate an additional key for the device to wirelessly communicate with an additional device.

3. The device of claim 2, wherein the processor is further configured to generate an additional secure package containing the key and to send the additional secure package wirelessly to the additional device to request wireless communications with the additional device.

4. The device of claim 1, wherein the extracting the contents of the secure package comprises at least one of decrypting the secure package, applying an inverse hash function to the secure package or reversing an obfuscation of the secure package.

5. The device of claim 1, wherein the extracting the contents of the secure package comprises extracting the key from the secure package.

6. The device of claim 1, wherein the extracting the contents of the secure package comprises at least one of extracting a timestamp.

7. The device of claim 6, wherein the validating the key comprises using the timestamp to determine whether the key has expired.

8. The device of claim 1, wherein the extracting the contents of the secure package comprises extracting information regarding rights to be granted to the device as to wireless communications.

9. A glucose monitor, comprising:
a wireless transceiver for transmitting and receiving wireless communications;
a processor configured to:
receive a secure package from a device via a wireless connection;
extract contents of the secure package, including a key;
validate the key as valid or not;
where the key is valid, in view of contents of the secure package, grant only viewing rights to the device so that the device can read information from the glucose monitor but is prohibited from changing values stored at the glucose monitor and from issuing commands to the glucose monitor; and
where the key is not valid, not permit wireless communications with the medicament delivery device.

10. The glucose monitor of claim 9, wherein the extracting the contents of the secure package comprises at least one of decrypting the secure package, applying an inverse hash function to the secure package or reversing an obfuscation of the secure package.

11. The glucose monitor of claim 9, wherein the extracting the contents of the secure package comprises extracting the key from the secure package.

12. The glucose monitor of claim 9, wherein the extracting the contents of the secure package comprises at least one of extracting a timestamp.

13. The glucose monitor of claim 12, wherein the validating the key comprises using the timestamp to determine whether the key has expired.

14. The glucose monitor of claim 12, wherein the extracting the contents of the secure package comprises extracting information regarding rights to be granted to the medicament delivery device as to wireless communications.

15. The glucose monitor of claim 9, wherein the device is a wearable device or an on-body device.

16. The glucose monitor of claim 14, wherein the key specifies the rights of the device as to wireless communications as the viewing only rights.

* * * * *